United States Patent [19]

Takano et al.

[11] Patent Number: 5,567,851
[45] Date of Patent: Oct. 22, 1996

[54] CYCLOHEXENE DIOL DERIVATIVES

[75] Inventors: Seiichi Takano; Kunio Ogasawara, both of Sendai, Japan

[73] Assignee: Chisso Corporation, Osaka, Japan

[21] Appl. No.: 448,665

[22] Filed: May 24, 1995

Related U.S. Application Data

[62] Division of Ser. No. 251,260, May 31, 1994, Pat. No. 5,442,098.

[30] Foreign Application Priority Data

May 31, 1993 [JP] Japan ................................. 5-149822

[51] Int. Cl.$^6$ .................................................. C07C 45/41
[52] U.S. Cl. ........................ 568/354; 568/355; 435/135; 560/220; 560/256
[58] Field of Search ............................ 435/135; 568/354, 568/356; 560/220, 256

[56] References Cited

U.S. PATENT DOCUMENTS

| | | | |
|---|---|---|---|
| 5,021,345 | 6/1991 | Urban et al. | 438/135 |
| 5,032,523 | 7/1991 | Amano et al. | 435/135 |
| 5,232,843 | 8/1993 | Bosley et al. | 435/135 |
| 5,346,885 | 9/1994 | Mimoun et al. | |
| 5,387,514 | 2/1995 | Schudok et al. | 435/135 |

OTHER PUBLICATIONS

Seiichi Takano et al. "Enantiocontrolled Synthesis of Optically Pure 5-Trimethylilyl-and 5-Tributylstannyl-cyclohex-2-enones." J. Chem. Soc. Chem. Commun. 1993. pp. 778–789.

Morio Asaoka et al. "A New Enantioselective Approach to the Bicylo[4.4.0]decane and Bicyclo[4.3.0.]nonane System-."Bull. Chem. Soc. Jpn., 63, 407–411(1990).

Primary Examiner—James H. Reamer
Attorney, Agent, or Firm—Browdy and Neimark

[57] ABSTRACT

The present invention relates to optically active cyclohexene diol derivatives and optically active cyclohexenone derivatives, and a process for production of these compounds in which a special cyclohexene diol of a starting material is reacted by selectively positioning transesterification in the presence of lipase to obtain an optically active cyclohexene diol derivative and then an optically active cyclohexenone derivative represented by the following formula:

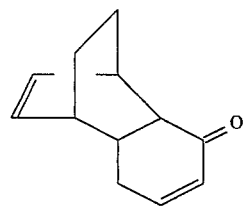

(2)

or

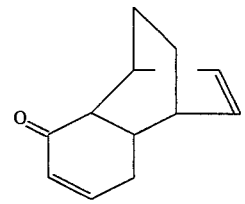

(2')

According to the present invention, optically active cyclohexene diol derivatives and optically-active cyclohexenone derivatives, which are intermediates for synthesizing physiologically active materials, can be obtained efficiently.

12 Claims, No Drawings

CYCLOHEXENE DIOL DERIVATIVES

This is a division of parent application Ser. No. 08/251,260 filed May 31, 1994, now U.S. Pat. No. 5,442,098.

BACKGROUND OF THE INVENTION

1. Field of the Invention

The present invention relates to the following optically active cyclohexene diol derivatives (1) and (1'), and optically active cyclohexenone derivatives (2) and (2'), and a process for production of these compounds.

2. Description of the Prior Art

The optically active cyclohexene diol derivatives represented by the following formula (1) and (1'), and the optically active cyclohexenone derivatives represented by the following formula (2) and (2') are useful as intermediates for synthesizing physiologically active compounds.

The optically active cyclohexenone derivatives represented by the formula (2), for example, can be used to obtain occidol (8) of a sesquiterpene through six steps as shown in the following.

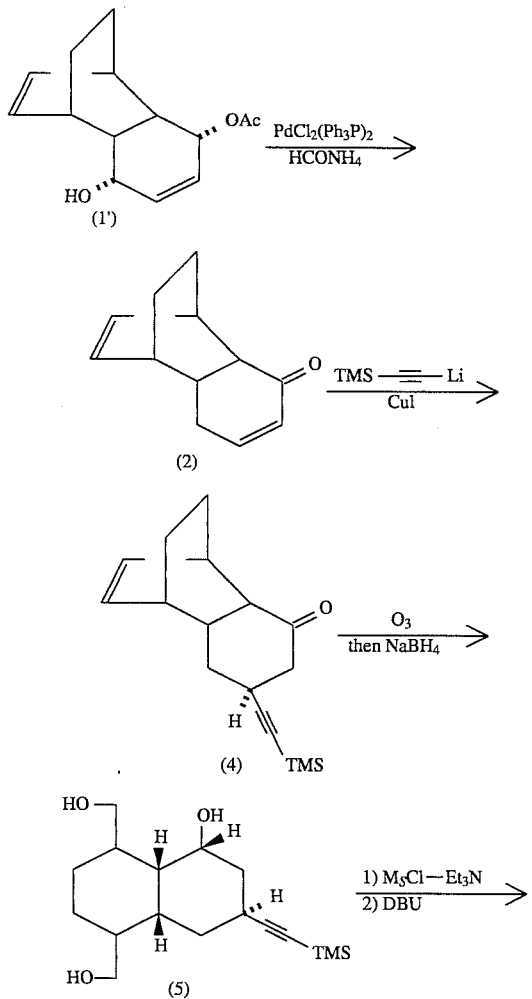

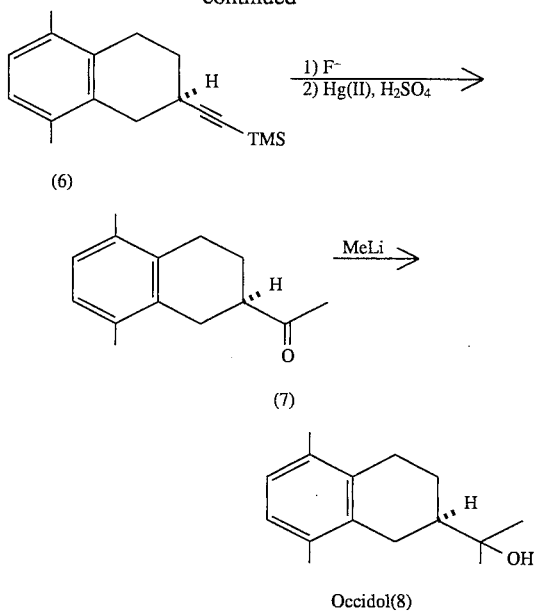

Further, the optically active cyclohexene diol derivative represented by the formula (1) can be an intermediate for synthesizing compactin (19) which is a hyperlipemia therapeutic drug (HMG CoA reductase synthesis inhibitor) as shown in the following.

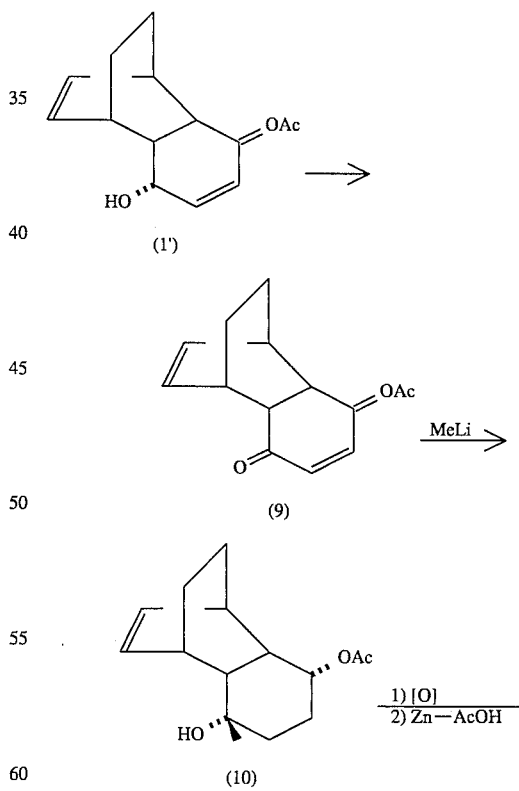

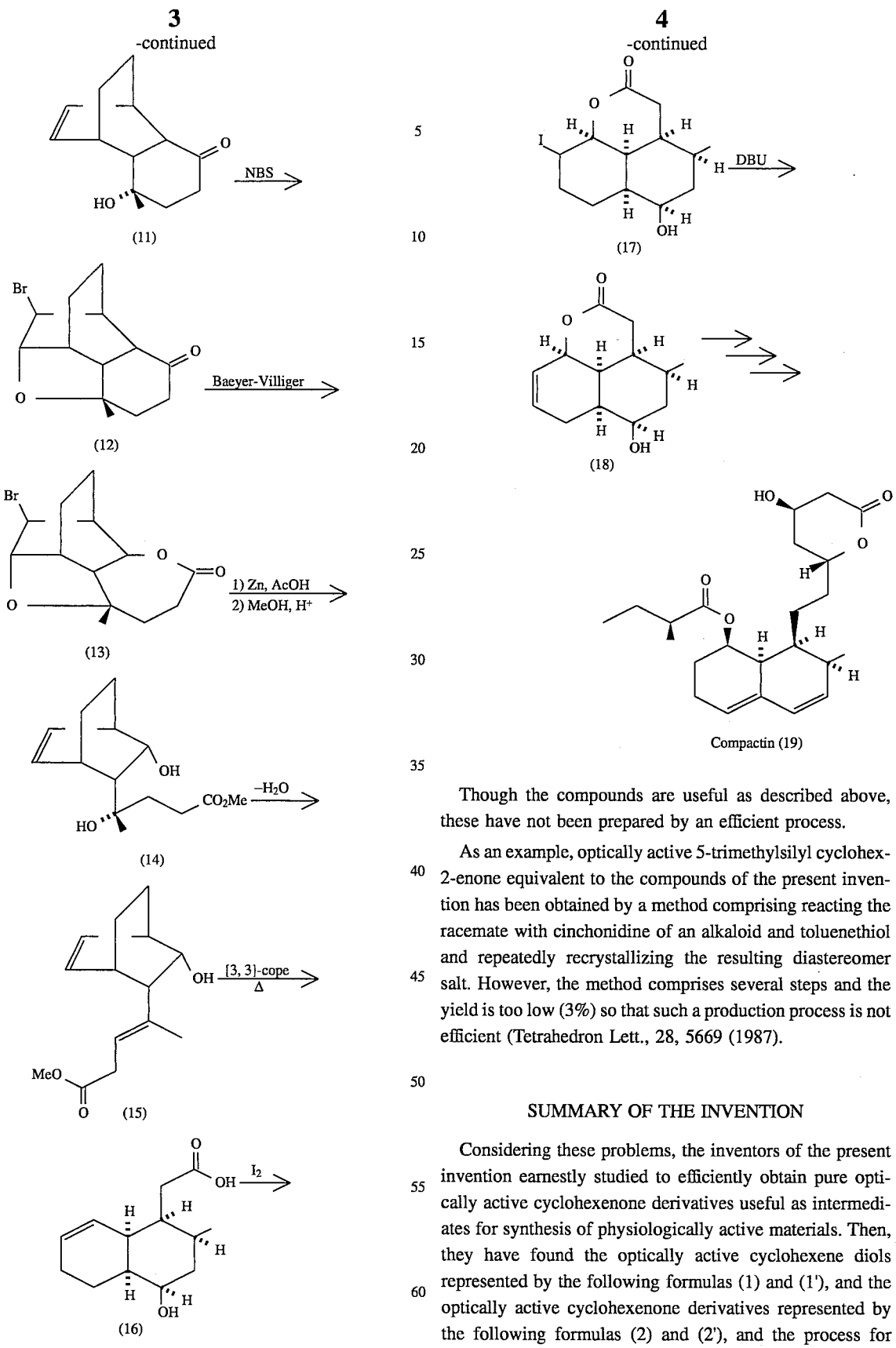

Though the compounds are useful as described above, these have not been prepared by an efficient process.

As an example, optically active 5-trimethylsilyl cyclohex-2-enone equivalent to the compounds of the present invention has been obtained by a method comprising reacting the racemate with cinchonidine of an alkaloid and toluenethiol and repeatedly recrystallizing the resulting diastereomer salt. However, the method comprises several steps and the yield is too low (3%) so that such a production process is not efficient (Tetrahedron Lett., 28, 5669 (1987).

SUMMARY OF THE INVENTION

Considering these problems, the inventors of the present invention earnestly studied to efficiently obtain pure optically active cyclohexenone derivatives useful as intermediates for synthesis of physiologically active materials. Then, they have found the optically active cyclohexene diols represented by the following formulas (1) and (1'), and the optically active cyclohexenone derivatives represented by the following formulas (2) and (2'), and the process for efficiently producing these compounds.

The present invention is characterized in that a cyclohexene diol represented by the formula:

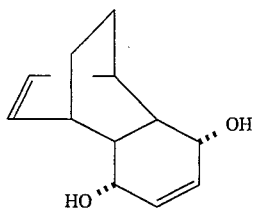
(3)

is used as a starting material to react with an acylating agent in the presence of lipase by selectively positioning transesterification, and an optically active cyclohexene diol derivative represented by the formula:

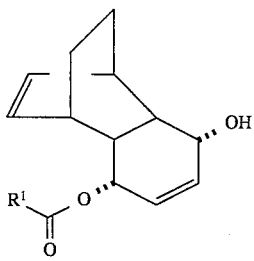
(1)

or

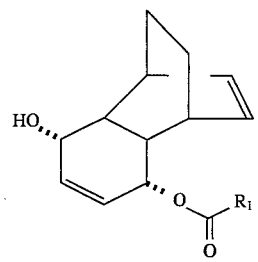
(1')

wherein $R_1$ is alkyl, is obtained from the above reaction, and then an optically active cyclohexenone derivative represented by the formula:

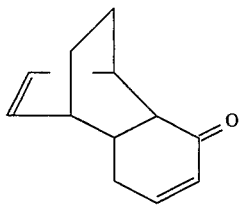
(2)

or

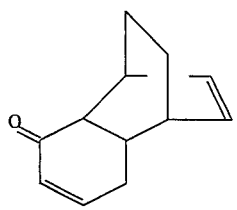
(2')

is obtained. The reaction steps of the production method of the present invention are shown in the following as an example.

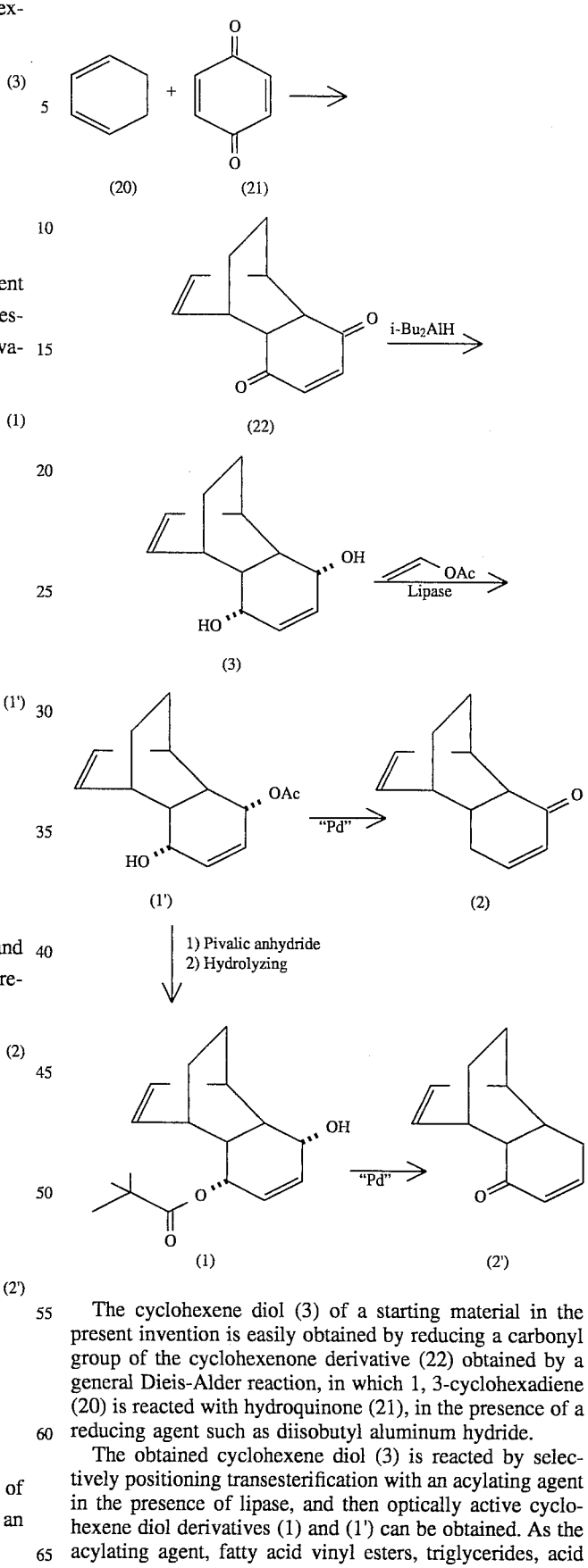

The cyclohexene diol (3) of a starting material in the present invention is easily obtained by reducing a carbonyl group of the cyclohexenone derivative (22) obtained by a general Dieis-Alder reaction, in which 1,3-cyclohexadiene (20) is reacted with hydroquinone (21), in the presence of a reducing agent such as diisobutyl aluminum hydride.

The obtained cyclohexene diol (3) is reacted by selectively positioning transesterification with an acylating agent in the presence of lipase, and then optically active cyclohexene diol derivatives (1) and (1') can be obtained. As the acylating agent, fatty acid vinyl esters, triglycerides, acid anhydrides, esters are exemplified, and fatty acid vinyl esters are preferred. As the lipase, if it acts as a catalyst, any kinds of lipase may be used in any forms of purified enzyme powder, immobilized enzyme, microorganisms and the like. Particularly, lipase from a Pseudomonas genus, for example, commercially available lipase PS (trade name, manufactured by Amano Pharmaceutical Co., Ltd. ) and TOYOBO lipase (trade name, manufactured by Toyobo Co., Ltd.) are preferred. As a reaction solvent, an organic solvent which does not inhibit the reaction can be preferably used, and more preferably acetonitrile is used. Otherwise, the reaction may be conducted in the presence of substrates without a solvent.

The optically active cyclohexene diol derivatives (1) and (1') can be converted into the optically active cyclohexenone derivatives (2) and (2') by using, for example, bistriphenylphosphine palladium chloride.

By the above described process, the following merits are obtained.

1. It is possible to obtain efficiently, as optically pure compounds, optically active cyclohexene diol derivatives and optically active cyclohexenone derivatives which are useful for synthesis of physiologically active materials.
2. The optically active cyclohexene diol derivatives and optically active cyclohexenone derivatives obtained by the process of the present invention can be converted to useful chiral elements. As described above, for example, these compounds may be starting materials of occidol (8) and compactin (19).
3. The cyclohexene diol represented by formula (3) is a meso compound, so that the optically active cyclohexene diol derivatives obtained from the compound can be act as both enantiomers by classification of hydroxy and acyl groups.

DESCRIPTION OF PREFERRED EMBODIMENTS

The following examples illustrate the present invention more specifically, but these are not intended as a definition of the limits of the invention.

EXAMPLE 1

To a solution of cyclohexene diol ( formula (3), 2 00 mg, 1.04 mmol) and vinyl acetate (0.3 ml, 3.36 mmol) in acetonitrile, lipase PS (100 mg) was suspended. The mixture was stirred for 25 days at room temperature. After the lipase was filtered off, the filtrate was concentrated under reduced pressure. The residue was subjected to a column chromatograph over silica gel to obtain colorless solid monoacetate (formula (1'), 202 mg, 83%). The specific rotation of the monoacetate was $[\alpha]_D^{30}$ −76.5° (c 1.02, CHCl$_3$). Further, the other physical property values were as follows.
IR (film) 3444 cm$^{-1}$, 1737 cm$^{-1}$ $^1$H-NMR (90 MHz ), CDCl$_3$
1.16–1.70 (m, 4H), 1.90 (s, 1H, D$_2$O exchangeable), 2.03 (s, 3H), 2.26 (ddd, 2H, J=7.1, 5.4, 1.7 Hz), 2.42–2.79 (m, 2H), 4.14 (quint, 1H, J=5.4 Hz), 5.39 (t, 1H, J=5.4 Hz), 5.96–6.48 (m, 4H)
MS
m/z 234 (M$^+$), 80 (100% )
HRMS
Calculated for C$_{14}$H$_{18}$O$_3$, 234.1256 (M$^+$), Found, 234.1240

EXAMPLE 2

To a solution (1 ml) of monoacetate (formula (1'), 146 mg, 0.624 mmol) in dichloromethane, triethylamine (0.35 ml, 2.5 mmol), DMAP (5 mg, 0.04 mmol) and pivalonic anhydride (0.38 ml, 1.9 mmol) were added. The mixture was stirred for three days at room temperature. After adding water, the mixture was extracted with dichloromethane. The organic layer was washed with a saturated aqueous solution of sodium bicarbonate and then with a saturated solution of sodium chloride, and dried over magnesium sulfate. The solvent was distilled away under reduced pressure. The residue was subjected to a chromatograph over silica gel to obtain a pivalate. The compound was dissolved in methanol (3 ml), and potassium carbonate was added and the mixture was stirred for one hour. Dichloromethane was added, and the mixture was washed with a saturated aqueous solution of sodium chloride twice and dried over magnesium sulfate. The solvent was distilled away under reduced pressure and the residue was subjected to a chromatograph over silica gel to obtain the colorless solid pivalate (formula (1), 152 mg, 88%). The specific rotation of the compound was $[\alpha]_D^{30}$ +99.3° (c 1.06, CHCl$_3$). The other physical property values were as follows.
m.p. 72°–73° C.
IR (nujol) 1731, 1695, 3488 cm$^{-1}$
$^1$H-NMR (90 MHz ), CDCl$_3$
1.17 (s, 9H), 1.17–1.55 (m, 4H), 1.62 (s, 1H), 2.04–2.78 (m, 4), 4.13 (quint, 1H, J=5.6 Hz), 5.29 (t, 1H, J=5.4 Hz), 6.00–6.46 (m, 4H)
MS
m/z 276 (M$^+$), 80 (100%) P0 HRMS
Calculated for C$_{17}$H$_{24}$O$_3$, 276.1725, Found, 276.1725

EXAMPLE 3

To a solution (2 ml) of a monoacetate (formula (1'), 100 mg, 0.427 mmol) in acetonitrile, ammonium carbonate (41 mg) and bistriphenylphosphine palladium chloride (3 mg, 0.004 mmol) were added, and the mixture was refluxed for 20 minutes. Diethyl ether was added to the reaction mixture. The solution was washed with a saturated aqueous solution of sodium bicarbonate and then with an aqueous solution of sodium chloride. The organic layer was dried over magnesium sulfate. The solvent was distilled away under reduced pressure. The residue was subjected to a chromatograph over silica gel to obtain the cyclohexenone derivative (62 mg, 84% ) represented by formula (2). The physical property values were as follows. The specific rotation of the compound was $[\alpha]_D^{32}$ −147° (c 0.41, CHCl$_3$). The other physical property values were as follows.
m.p. 46.5°–47.5 ° C.
IR (nujol) 1650 cm$^{-1}$
$^1$HMR (90 MHz ), CDCl$_3$
1.11–1.69 (m, 4H), 1.73–2.26 (m, 1H), 2.27–2.67 (m, 4H), 3.09 (br. s, 1H), 5.79 (ddd, 1H, J=10.2, 2.5, 1.7 Hz), 6.03–6.35 (m, 2H), 6.56–6.78 (m, 1H)
MS
m/z 174 (M$^+$), 80 (100%)
HRMS Calculated for C$_{12}$H$_{14}$O, 174.1045, Found, 174.1059

EXAMPLE 4

The same method as in Example 3 was used except that pivalate (formula (1), 99 mg, 0.359 mmol), ammonium carbonate (34 mg, 0.54 mmol), triphenylphosphine palladium chloride (2.5 mg, 0.0035 mmol) and acetonitrile 3 mg were used to obtain the cyclohexenone derivative (formula (2'), 49 mg, 79%). The specific rotation was $[\alpha]_D^{31}$ +144.6° (c 0.418, CHCl$_3$). The melting point was as follows.
m.p. 46°–47° C.

In addition, the optical purity was>99% ee by using optical resolution HPLC (trade name, CHIRAL CEL OB, effluent: i-PrOH/hexane=⅑).

We claim:

1. A process for producing an optically active cyclohexene diol derivative represented by the general formula (1) or (1')

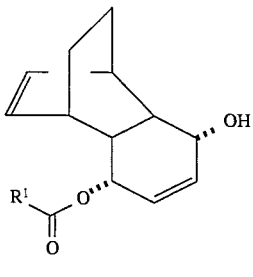
(1)

or

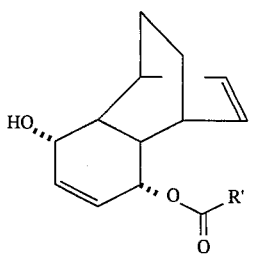
(1')

where R'is alkyl, comprising reacting by selectively positioning transesterification a cyclohexene diol as a starting material represented by the formula:

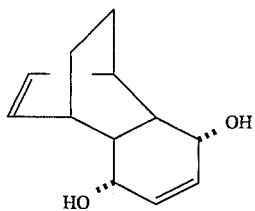
(3)

with an acylating agent in the presence of lipase, and obtaining the said optically active cyclohexene diol derivative.

2. A process for producing an optically active cyclohexanone derivative represented by the formula

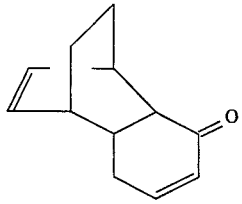
(2)

or

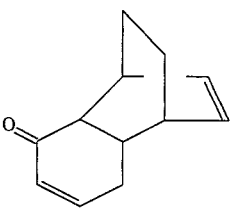
(2')

comprising the step of converting the optically active cyclohexene diol derivative of claim 1, represented by formula (1) or (1'), to said optically active cyclohexanone derivative of formula (2) and (2')in the presence of a palladium complex as catalyst.

3. The process in accordance with claim 1, wherein said acylating agent is selected from the group consisting of fatty acid vinyl esters, triglycerides, acid anhydrides, and esters.

4. The process in accordance with claim 3, wherein said acylating agent is a fatty acid vinyl ester.

5. The process in accordance with claim 1, wherein said lipase is a lipase obtainable from a microorganism from the Pseudomonas genus.

6. The process in accordance with claim 1, wherein said reacting step takes place at room temperature.

7. The process in accordance with claim 2, wherein said converting step involves refluxing a mixture of an optically active mixture of cyclohexene diol derivative of formula (1) or (1'), ammonium carbonate and a palladium complex.

8. The process in accordance with claim 2, further comprising the step of obtaining said optically active cylcohexanone derivative of formula (2) or (2').

9. The process in accordance with claim 8, wherein said step of obtaining said optically active cylcohexanone derivative of formula (2) or (2') comprises washing with an aqueous solution, and drying.

10. The process in accordance with claim 9, wherein said step of obtaining said optically active cylcohexanone derivative of formula (2) or (2') further comprises the steps of adding a solvent and distilling off said solvent.

11. The process in accordance with claim 10, wherein said solvent is diethyl ether.

12. The process in accordance with claim 2, wherein said palladium complex as catalyst is selected from the group consisting of bistriphenyl phosphine palladium chloride and triphenyl phosphine palladium chloride.

* * * * *